United States Patent
Yamamoto et al.

(10) Patent No.: US 6,734,016 B1
(45) Date of Patent: May 11, 2004

(54) METHOD FOR CULTURING CELL AND A CULTURE VESSEL

(75) Inventors: Nobutaka Yamamoto, Kasugai (JP);
Akihisa Sugiyama, Kasugai (JP);
Satoshi Kawaminami, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 09/718,388

(22) Filed: Nov. 24, 2000

(30) Foreign Application Priority Data

Nov. 26, 1999 (JP) ............................................ 11-336208
Nov. 26, 1999 (JP) ............................................ 11-336210

(51) Int. Cl.$^7$ ................................................ C12N 5/08
(52) U.S. Cl. ........................ 435/371; 435/391; 435/402
(58) Field of Search ............................... 435/347, 85.1, 435/173.1, 373, 391, 367, 352, 371, 402

(56) References Cited

U.S. PATENT DOCUMENTS 4,016,036 A * 4/1977 Green et al.
4,940,666 A * 7/1990 Boyce et al. ............... 435/371

FOREIGN PATENT DOCUMENTS

| EP | 0 168 217 | 1/1986 |
| JP | 62-285781 | 12/1987 |
| WO | 0 168 217 | * 4/1985 |

OTHER PUBLICATIONS

Rheinwald et al. Epidermal growth factor and the multiplication of cultured human epidermal keratinocytes. Nature vol. 265 197 pp. 421–424.*

Todaro et al. Quantitative studies of the growth of mouse embryo cells in culture and their development into established lines pp. 299–312 (no date).*

Rheinwald, James, et al.; "Serial Cultivation of Strains of Human Spidermal Keratinocytes: The Formation of Keratinizing Colonies From Single Cells"; Cell, vol. 6, pp. 331–334; Nov. 1975.

Summary of Ishizaka, T. et al.; "In Vitro Development and Functions of Human Mast Cells"; Int. Arch Allergy Appl. Immunol; 1991; 94; (1–4); 116–21.

Summary of Doetschman, T. et al.; "Establishment of Hamster Blastocyst–Derived Embryonic Stem (ES) Cells" Dev. Biol.; May 1998, 127 (1); 224–227.

Torado et al.—"*Quantitative Studies of the Growth of Mouse Embryo Cells in Culture and Their Development into Established Lines*"—The Journal of Cell Biology, vol. 17, 1963, pp. 299–312.

Document 2, Translation of p. 54, lines 26–27—"3T3 Cell".

Document 3, Translation of p. 37, lines 9–13.

Document 4, Translation of p. 348, lines 22–31.

* cited by examiner

*Primary Examiner*—James Ketter
(74) *Attorney, Agent, or Firm*—Armstrong, Kratz, Quintos, Hanson & Brooks, LLP

(57) ABSTRACT

A method for adhering and proliferating cell, which comprises the steps of inoculating, culturing and then killing fibroblast derived from a mammal, is provided. A culture vessel manufactured according to the steps of the method which can provide improved adhesion to cell and enhanced cell-proliferation is also provided.

11 Claims, 1 Drawing Sheet

METHOD FOR CULTURING CELL AND A CULTURE VESSEL

BACKGROUND OF THE INVENTION

The present invention relates to a method for adhering and proliferating cell. Particularly, the present invention relates to a method for adhering and proliferating epithelial and hepatic cell. The present invention also relates to a method for culturing epidermal cell to be used in an epidermal cell sheet and an epidermal cell suspension which can be applied to an apellous part such as those with burn, wound, bedsore or skin ulcer for early reconstruction or treatment of such damaged tissue, an epidermal cell sheet and suspension prepared by the culture method, and a method for culturing hepatic cell which is important in analysis of hepatic function.

The present invention also relates to a culture vessel manufactured according to the steps of the methods of the present invention, which can provide improved adhesion to cell and enhanced cell-proliferation. Particularly, the present invention relates to a culture vessel which can provide improved adhesion to epithelial and/or hepatic cell and enhanced epithelial and/or hepatic cell-proliferation. More particularly, the present invention relates to a culture vessel that enables preparation of an epidermal cell sheet and an epidermal cell suspension to be applied to an apellous part such as those with burn, wound, bedsore or skin ulcer for early reconstruction or treatment of such damaged tissue.

Conventionally, two methods have widely been employed for culturing epithelial cell, particularly epidermal cell (or which is called epidermal keratinocyte). One utilizes sterilized 3T3 mouse embryo fibroblast, i.e., viable 3T3 mouse embryo fibroblast from which division and proliferation potencies have been deleted by irradiating, for example, γ ray or by adding an agent such as mitomycin C, as feeder layer (such as the feeder layer culture method described in James G. Rheinwald and Howard Green. Cell 6:331–344. Serial Cultivation of Strains of Human Epidermal Keratinocytes: the Formation of Keratinizing Colonies from Single Cells). The other utilizes serum-free medium such as MCDB153 instead of feeder layer.

However, the conventional feeder layer culture method in which 3T3 mouse embryo fibroblasts are used as a feeder layer involves complicated procedure for preparing the 3T3 mouse embryo fibroblasts immediately before epidermal cells are inoculated, and such feeder layer has a limited life time. During proliferation of epidermal cells other than mouse epidermal cells such as human epidermal cells and preparation of an epidermal cell sheet, those cells may possibly be contaminated with heterogenous cells, 3T3 mouse embryo fibroblasts, and an agent such as mitomycin C, which is added to delete division and proliferation potencies of the 3T3 embryo fibroblasts, may remain.

On the other hand, when fibroblast homogenous to the epidermal cell and/or epidermal cell sheet of interest is used as the feeder cell instead of 3T3 mouse embryo fibroblast (e.g., human fibroblast may be used for preparing a human epidermal cell sheet), there is no possibility of contamination with heterogenous cells. However, their division and proliferation potencies should also be deleted by adding an agent such as mitomycin C that may possibly remain. Human fibroblast may be used, but they provide slower proliferation rate of the epidermal cells when compared to that obtained by using 3T3 mouse embryo fibroblast.

Culture method employing serum-free medium may often provide slower proliferation rate of epidermal cell and require longer period of time for incubation when compared to feeder layer culture methods which employ feeder cells such as 3T3 mouse embryo fibroblast. Further, serum-free medium is likely to suppress the differentiation of epidermal cell, which may cause inability of the epidermal cell to form a multiple-layer, resulting in unsuccessful preparation of an epidermal cell sheet.

Japanese Unexamined Patent Application Publication No. 285781/1987 disclosed a method which employs a feeder layer to culture hepatic cells. This method may also have a possibility of residual agent or contamination with heterogenous cells. Further, this method requires continual subculture of feeder cell to keep the cell ready for use under an optimal condition (subconfluent), making the procedure very complicated.

SUMMARY OF THE INVENTION

According to the investigation of various culture conditions for epidermal cell forming an epidermal cell sheet and hepatic cell, a novel method is found, which comprises the steps of inoculating, culturing and then killing fibroblast derived from a mammal and separating the killed fibroblasts from the vessel at least partially to substantially leave a component or components, on the surface of the culture vessel, such as the accumulated extracellular matrix which has been secreted from the culture cells. Thus, this method does not require preparing feeder cells such as fibroblasts nor sterilizing the cells as required in conventional feeder layer culture methods. Further, a culture vessel manufactured according to the steps of the above method, which can provide improved adhesion to cell and enhanced cell-proliferation, may enable to be preserved for long time while keeping its property. Accordingly, the culture vessel does not require daily subculture (i.e., transferring cells on another vessel in order to prevent overpopulation of the cells in the culture vessel) of fibroblasts to be used as the feeder cells. Preservation of a large stock of the culture vessels can be preserved in a cold and dark place. Further, the culture vessel which can provide improved adhesion to cell and enhanced cell-proliferation when compared to one manufactured by conventional methods can be obtained. On the basis of these findings, the present invention has been completed.

Accordingly, one object of the present invention is to provide a method for adhering and proliferating cell comprising the steps of inoculating, culturing and then killing fibroblast derived from a mammal, which can provide improved cell adhesion and proliferation potencies when compared to those provided by conventional feeder layer culture method, without preparing feeder cells such as fibroblasts nor sterilizing such cells as required in conventional feeder layer culture methods, and thus can provide an epidermal cell sheet, an epidermal cell suspension or hepatic cells while avoiding contamination with heterogenous cells. Another object of the present invention is to provide the followings: a method for culturing epidermal cell to be used in an epidermal cell sheet and an epidermal cell suspension which can be applied to an apellous part such as those with burn, wound, bedsore or skin ulcer for early reconstruction or treatment of the damaged tissue; an epidermal cell sheet and an epidermal cell suspension prepared by the culture method; and a method for culturing hepatic cells which is important in analysis of hepatic function.

Still another object of the present invention is to provide a culture vessel which can provide improved adhesion to cell and enhanced cell-proliferation according to the steps of the above method. Particularly, one object of the present invention is to provide a culture vessel which can provide improved adhesion to cell and enhanced cell-proliferation, which are manufactured by culturing and killing fibroblasts derived from a mammal (particularly 3T3 mouse embryo fibroblast) by, for example, freezing and/or drying in a culture vessel and separating the killed fibroblasts from the vessel at least partially to substantially leave a component or components such as the accumulated extracellular matrix which has been secreted from the culture cells to remain on the surface of the culture vessel, i.e., to leave component(s) necessary for cell adhesion and proliferation to remain on the surface of the culture vessel.

In summary, the present invention relates to a method for adhering and proliferating cell which comprises the steps of inoculating, culturing and then killing fibroblast derived from a mammal.

In the method, killed fibroblast may be preferably separated from the vessel partially, and more preferably entirely.

In the method, fibroblast may be killed by freezing, drying and/or irradiating electromagnetic radiation or by repeating one treatment selected from the group consisting of freezing, drying and irradiating electromagnetic radiation. Fibroblast may also be killed by a combination of at least two treatments selected from the group consisting of freezing, drying and irradiating electromagnetic radiation. In the method, electromagnetic radiation may be at least one selected from the group consisting of β ray, γ ray, X-ray, electron beam and UV ray.

In the method, 3T3 mouse embryo fibroblast may be used as fibroblast derived from a mammal.

In the method, epithelial or hepatic cell may be used as the cell which adheres and proliferates. Epidermal cell is preferable as epithelial cell.

Further, the present invention relates to epidermal cell which has been cultured using the method. The present invention also relates to an epidermal cell sheet or suspension prepared from the epidermal cell.

The present invention also relates to a culture vessel manufactured according to the steps of the method, which can provide improved adhesion to epithelial and/or hepatic cell and enhanced epithelial and/or hepatic cell-proliferation.

In the culture vessel, killed fibroblast may be preferably separated at least partially, or entirely.

Preferably, the culture vessel can be preserved by freezing and/or drying.

For the culture vessel, 3T3 mouse embryo fibroblast is used as fibroblast derived from a mammal preferably.

For the culture vessel, epidermal keratinocyte may be used preferably as the epithelial cell.

The material of the culture vessel may be glass, synthetic polymer or biopolymer. Further, the culture vessel may have any shape such as flask, petri dish, roller bottle, tray, well plate, beads, film, sheet or sponge.

The culture vessel made of glass or synthetic polymer may have any shape such as flask, petri dish, roller bottle, tray, well plate, beads, film, sheet or sponge.

Preferably, the culture vessel made of biopolymer may have any shape such as sheet, film, sponge or beads.

The culture vessel may be used to prepare an epidermal cell sheet.

The culture vessel may be used to prepare an epidermal cell suspension.

DETAILED DESCRIPTION

Figure 1:
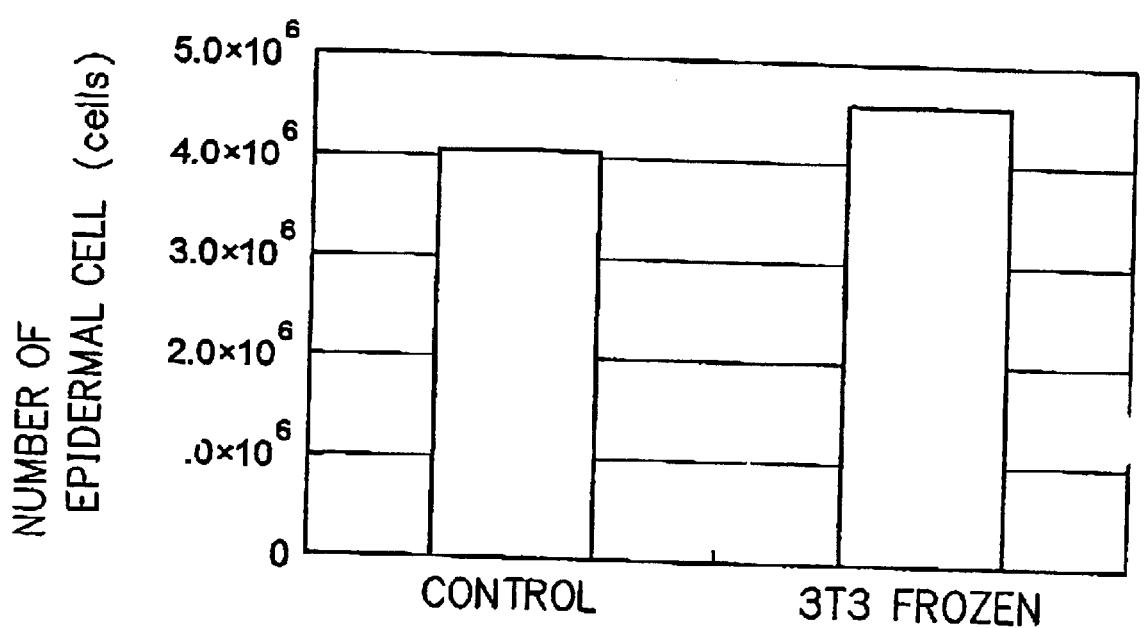
FIG. 1 illustrates a bar graph showing the average number of epidermal cells collected from each of the culture flasks (culture surface: 25 cm$^2$) of frozen 3T3 and the control in Example 1 in triplicate by performing the test in triplicate.

Cells to adhere and proliferate in the cell adhesion and proliferation method according to the present invention include those that can be cultured by any conventional feeder layer culture method, such as epithelial cells and hepatic cell. The term "epithelial cell" herein encompasses the followings: epithelial cells such as mucosal epithelial cells (which are surface cells of intestine, oral cavity or nasal cavity) and corneal epithelial cells; and epidermal cells which exist on skin epithelium and are denucleated and keratinized after cell division. Hepatic cells are cells that constitute a hepatic lobule.

For the cell adhesion and proliferation method according to the present invention, it is important to kill fibroblast derived from a mammal after culturing them separate from the vessel in order to remove the killed fibroblasts at least partially, and leave extracellular matrix required for cell adhesion and proliferation on the surface of the culture vessel.

Fibroblasts may be used those derived from mammals such as mouse, human, rat, hamster and rabbit. Preferably, 3T3 mouse embryo fibroblast, which is commonly used in conventional feeder layer culture methods, may be used. The condition for inoculating and culturing cell is not particularly limited, and any standard condition may be used. For example, fibroblasts grown in a culture vessel may be separated by treating with trypsin solution (which was prepared by dissolving trypsin (0.25 weight/volume %) in a solution of 0.206 mg/ml ethylenediamine-tetraacetic acid (EDTA) in phosphate buffer). The separated fibroblasts were suspended in a medium supplemented with 5 to 10% fetal bovine serum, inoculated in the culture vessel, and then left to stand in a $CO_2$ incubator. No special culture vessel, for example, a culture vessel coated with extracellular matrix such as collagen, is required. Any material or shape may be used for the culture vessel as long as 3T3 fibroblasts, for example, can adhere to and proliferate in the culture vessel. Any culture vessel for adhesive cell which are commercially available such as flask, petri dish, roller bottle, well plate or tray, or any carriers such as conventional synthetic polymer membrane, film or plate, or biopolymer membrane, film or microbeads may be used, which can greatly reduce the process costs when compared to any conventional methods.

An embodiment of culture vessel will be described which can provide improved adhesion to cell and enhanced cell-proliferation according to the steps of the cell adhesion and proliferation method which comprises the steps of inoculating, culturing and then killing fibroblast derived from a mammal.

Fibroblasts are grown in a culture vessel and the grown fibroblasts are killed. The killed fibroblasts (hereinafter referred to as "dead cells") are then removed by separation, and component or components required for cell adhesion and proliferation are left on the surface of the culture vessel. As a result, property which can provide improved adhesion to cell and enhanced cell-proliferation will be rendered to the surface of the culture vessel. For the purpose of rendering such property to the surface of the culture vessel, fibroblasts are inoculated preferably at $1.0 \times 10^2$ to $1.0 \times 10^5$ cells/cm$^2$, and more preferably at $3.0 \times 10^3$ to $1.0 \times 10^5$ cells/cm$^2$, and then cultured under the above conditions.

In the subsequent step of killing the fibroblasts, it is important to kill substantially all the fibroblasts under the condition which may not degenerate the component or components required for cell adhesion and proliferation. Killing substantially all the fibroblasts may facilitate and ensure the removal of the fibroblasts. Thus, contamination of the resultant epidermal cell sheet, epidermal cell suspension or hepatic cells with heterogenous cells can be prevented. Further, unlike conventional sterilization such complete killing may not require adding an agent such as mitomycin C, thus avoiding possibility of residual agent.

Fibroblasts may be killed by any method that may not degenerate the component or components required for cell adhesion and proliferation nor inhibit the cell adhesion and proliferation. Such methods include freezing, freeze-drying, drying, drying at low temperature, irradiation of electromagnetic radiation such as β ray, γ ray, X-ray, electron beam and UV ray, and a combination of such treatments. These methods can retain the property of the culture vessel which can provide improved adhesion to cell and enhanced cell-proliferation. When epidermal cells are inoculated and cultured in such a culture vessel, they may adhere and proliferate well to prepare an epidermal cell sheet for practical use.

Fibroblasts may be preferably killed by freezing and drying. Freezing may be easily manipulated, and can kill a large number of fibroblasts at one time. Further, an apparatus to be used for freezing is generally cheaper than that used in other methods. After fibroblasts are killed, the culture device can be continually frozen for long-time preservation while retaining its property which can provide improved adhesion to cell and enhanced cell-proliferation. Freezing treatment may comprise freezing and thawing, or repeated freezer-thawing procedure. Freezing treatment includes freezer-dryer, freezer, ultra-deep freezer, liquefied $CO_2$ or liquefied nitrogen gas. Any freezing temperature may be used which can freeze cells. Usually, 0° C. or lower may be used. Preferably, fibroblasts may be gradually frozen by using, for example, a programmable freezer since freezing rate may affect the death of fibroblasts.

For drying treatment, any conventional dryer may be used. Drying temperature may be preferably from non-freezing temperature (around 0° C.) to 60° C., and more preferably 4° C. to 30° C. As described above, it is important to inhibit degeneration of active component(s). Therefore, fibroblasts may be desirably killed under these moderate conditions.

Fibroblasts may also be killed by irradiating electromagnetic radiation selected from the group consisting of electron beam, γ-ray and UV-ray. Preferable range of irradiating electron beam or γ-ray is 5 to 30 kGy, and preferable range of irradiating UV-ray is 50 to 5000 mW·sec/cm$^2$. For the purpose of rendering property which can provide improved adhesion to cell and enhanced cell-proliferation to the surface of the culture vessel, fibroblasts are inoculated preferably at $1.0 \times 10^2$ to $1.0 \times 10^5$ cells/cm$^2$, and more preferably at $1.0 \times 10^3$ to $1.0 \times 10^5$ cells/cm$^2$, and then cultured under the above conditions.

After culturing, culture supernatant of the fibroblast is removed, and then the remainder is treated by irradiating 5 to 30 kGy electron beams. Before irradiating electron beam or γ-ray, i.e., after culture supernatant of the fibroblast is removed, the culture vessel is preferably kept at most 4° C. More preferably, a culture vessel is treated by irradiating ray after freezing treatment. Such conditions of the treatment prevent component or components required for cell adhesion and proliferation from degeneration. When a vessel is treated by irradiating electron beam keeping at 4° C., for example, adhesion to cell and cell-proliferation are a little inferior when compared to feeder layer culture methods. However, an equivalent epidermal cell sheet can be prepared when compared to that obtained according to feeder layer culture methods. In the culture vessel which is treated by irradiating ray after freezing treatment, adhesion to cell and cell-proliferation are equal when compared to feeder layer culture methods. Irradiating electron beam or γ-ray is useful to kill fibroblast completely and sterilize a culture vessel.

After fibroblasts are killed by the above treatment, dead cells are removed by separation. The term "separate" or "separation" herein intends to encompass all the manipulations for removing dead cells such as detaching or washing.

In this process, fibroblasts should be completely removed in order to prevent heterogenous cells such as 3T3 mouse embryo fibroblast from contaminating the epidermal cell sheet, epidermal cell suspension or hepatic cells obtained by using the culture vessel manufactured according to the steps of the above cell adhesion and proliferation method, which comprises inoculating, culturing and then killing fibroblast derived from a mammal to provide improved cell adhesion and proliferation. However, complete removal of fibroblasts may not always be necessary in the aspect of cell adhesion and proliferation. Accordingly, the dead cells may be removed at least partially such that cell adhesion or proliferation may not be inhibited. The term "be separated at least partially" herein, which refers to the extent of removal of dead cells, particularly means removing preferably 50% or more, more preferably 80% or more, and most preferably 100% of dead cells when compared to the total amount of viable fibroblasts just before killed.

Dead cells may be generally removed by rinsing the culture surface with any isotonic solution which does not degenerate the active component or components required for cell adhesion and proliferation, such as phosphate buffer, Hanks' solution and saline.

The extent to which dead cells are removed can be easily confirmed by using, for example, a phase contrast microscope. When 100% removal of dead cells is confirmed, then it means that the resultant epidermal cell sheet, epidermal cell suspension or hepatic cells are free of heterogenous cells such as 3T3 mouse embryo fibroblast. It is not difficult to remove 100% of dead cells. Dead cells can be easily removed almost completely by any conventional procedure. Alternatively, dead cells will completely be apart from the surface of the vessel into the culture solution. Therefore, an epidermal cell sheet, an epidermal cell suspension or hepatic cells obtained by using the culture vessel according to the present invention which can provide improved adhesion to cell and enhanced cell-proliferation may be substantially free of any heterogenous cell. Conventionally, a practical epidermal cell sheet could be prepared only be feeder layer culture method which may cause contamination with heterogeneous cells to some extent when cells derived from a mammal other than human are used as the feeder cells. On the other hand, an epithelial cell sheet, i.e., a muscosa epithelial cell sheet or a muscosa epithelial cell suspension, or an epidermal cell sheet or an epidermal cell suspension obtained by using the culture vessel according to the present invention which can provide improved adhesion to cell and enhanced cell-proliferation are free of heterogeneous cells.

The culture vessel which can provide improved adhesion to cell and enhanced cell-proliferation (e.g., a petri dish containing component(s) required for adhesion and proliferation of the target cell from the surface of which dead cells have been removed) can be left to stand, for example, in a refrigerator at 2° C. to 8° C. or in a deep freezer at −30° C., −80° C. or the like for at least about 0.5 to 1 year while keeping its property. This can eliminate several steps such as preparing a feeder layer just before inoculating of epidermal cells, deleting division potency of, for example, 3T3 fibroblasts by irradiating γ-ray or by adding mitomycin C and thereafter inoculating the cells ($1 \times 10^4$ cells/cm$^2$). Further, conventional feeder layers could retain their property only for about 2 days. On the other hand, the culture vessel according to the present invention, which can provide improved adhesion to cell and enhanced cell-proliferation, can be preserved for about 0.5 to 1 year while retaining such property. Moreover, a large number of the culture vessel according to the present invention can be easily manufactured at one time, and they can provide similar activity. Thus the process costs can be greatly reduced. Additionally, the method according to the present invention does not require daily subculture of fibroblasts for preparation of feeder layer.

The above epidermal cell sheet can be easily prepared in a desired amount when required, by using the culture vessel according to the present invention. Particularly such an epidermal cell sheet may be prepared by a method similar to any conventional process for preparing epidermal cell sheet except for using the culture vessel according to the present invention. For example, epidermal cells are inoculated ($1.0 \times 10^4$ cells/cm$^2$) and then cultured for about 7 to 21 days while changing the medium about twice a week to prepare an epidermal cell sheet.

The above epidermal cell suspension can be prepared by any conventional method for preparing epidermal cell suspension except for using the culture vessel according to the present invention. For example, epidermal cells are inoculated ($1.0 \times 10^4$ cells/cm$^2$) and then cultured for about 3 to 21 days while changing the medium about twice a week. Thereafter, the cells are treated with an enzyme such as trypsin to substantially obtain single cells which are then suspended in a solution such as neutral collagen solution.

Hereinafter, the present invention will be explained by way of following examples. These examples are not intended to limit the scope of the present invention.

EXAMPLE

Example 1

Established 3T3 mouse embryo fibroblasts were inoculated in a culture flask (culture surface: 25 cm$^2$) at $3 \times 10^3$ cells/cm$^2$ and incubated in a $CO_2$ incubator (at 37° C., 5% $CO_2$) for 4 days. The medium was Dulbecco's modified Eagle medium supplemented with 10% fetal bovine serum (DMEM+10%FBS).

After incubation, culture supernatant in the culture flask was removed by aspiration, and the remainder was left to stand in a deep freezer at −85° C. for 12 hours for freezing. Next, the frozen culture was thawed at room temperature, and the culture surface was rinsed with 5 ml of phosphate buffer to remove dead cells. Then, the culture flask was again frozen by leaving it to stand in the deep freezer at −85° C. overnight.

The culture flask (hereinafter referred to as "3T3 frozen") was thawed at room temperature and inoculated with epidermal cells ($1 \times 10^4$ cells/cm$^2$) collected from human skin.

On the other hand, epidermal cells were inoculated at $1 \times 10^4$ cells/cm$^2$ in a culture flask (culture surface; 25 cm$^2$) containing a feeder layer consisting of 3T3 mouse embryo fibroblasts which have been treated with mitomycin C to delete their division potency as a control.

These culture flasks were incubated in a $CO_2$ incubator (37° C. 5% $CO_2$) for 8 days. The medium was Green medium supplemented with 3% fetal bovine serum (Green+ 3%FBS).

After 8-day incubation, an epidermal cell sheet was prepared on the surface of each culture vessel. The sheet was separated from the culture surface of each culture vessel by treating with dispase, the epidermal cells were treated with trypsin solution (which was prepared by dissolving trypsin (0.25 weight/volume %) in a solution of 0.206 mg/ml ethylenediamine-tetraacetic acid (EDTA) in phosphate buffer) to obtain single cells, and the cells were counted on a hemacytometer.

The dispase treatment was performed by dissolving 10,000PU dispase in 10 ml of Dulbecco's modified Eagle medium to prepare dispase solution, adding 3 ml of the dispase solution to the culture flask, and leaving the flask to stand in a $CO_2$ incubator for about 1 hour.

Epidermal cells were counted for both the control and 3T3 frozen in triplet, and the average of the results were shown in FIG. 1 for comparison. As shown in FIG. 1, more epidermal cells were adhered and proliferated in the culture vessel according to the present invention (3T3 frozen) when compared to those grown by inoculating epidermal cells according to the conventional feed layer culture method (control), which employed 3T3 mouse embryo fibroblast as feeder cell, and incubating for 8 days.

Example 2

Established 3T3 mouse embryo fibroblasts were inoculated in a culture flask (culture surface: 25 cm$^2$) at $3 \times 10^3$ cells/cm$^2$ and incubated in a $CO_2$ incubator (at 37° C., 5% $CO_2$) for 4 days. The medium was Dulbecco's modified Eagle medium supplemented with 10% fetal bovine serum (DMEM+10%FBS).

After incubation, culture supernatant in the culture flask was removed by aspiration, and the remainder was freeze-dried in a freeze dryer. Schedule used was as follows: retaining at −30° C. for 1 hour; drying by vacuum aspiration; heating at 1.5° C./minute; and retaining at 20° C. for 20 hours.

Epidermal cells collected from human skin were inoculated in the culture flask at $1 \times 10^4$ cell/cm$^2$. The medium was Green medium supplemented with 3% fetal bovine serum. After 4 days, the colonies of epidermal cells were observed. The epidermal cells were proliferated without contamination with 3T3 mouse embryo fibroblasts.

Example 3

Established 3T3 mouse embryo fibroblasts were inoculated in a culture flask (culture surface: 25 cm$^2$) at $3 \times 10^3$ cells/cm$^2$ and incubated in a $CO_2$ incubator (at 37° C., 5% $CO_2$) for 4 days. The medium was Dulbecco's modified Eagle medium supplemented with 10% fetal bovine serum (DMEM+10%FBS).

After incubation, culture supernatant in the culture flask was removed by aspiration, and the remainder was left to stand in a deep freezer for 12 hours for freezing. Next, the frozen culture was thawed at room temperature, and the culture surface was rinsed with 5 ml of phosphate buffer to remove dead cells. Then, the culture flask was again frozen by leaving it to stand in the deep freezer at −85° C. overnight.

The culture flask (3T3 frozen) was thawed at room temperature and inoculated with epidermal cells collected from human skin at $1\times10^4$ cells/cm$^2$.

These culture flasks were incubated in a $CO_2$ incubator (37° C., 5% $CO_2$) for 8 days. The medium was Green medium supplemented with 3% fetal bovine serum (Green+ 3%FBS).

After 8-day incubation, epidermal cells were separated from the culture surface of each culture vessel, treated with trypsin solution (which was prepared by dissolving trypsin (0.25 weight/volume %) in a solution of 0.206 mg/ml ethylenediamine-tetraacetic acid (EDTA) in phosphate buffer) to obtain single cells, and then the cells were counted on a hemacytometer. $3\times10^5$ cells/ml epidermal cell suspension was prepared by suspending cells in a neutral collagen solution (which was prepared by dissolving aterocollagen derived from a hog (0.2 weight/volume %) in Dulbecco's modified Eagle medium, and by adjusting at pH 7.4).

Example 4

Established 3T3 mouse embryo fibroblasts wee inoculated in a culture flask (culture surface: 80 cm$^2$) at $3\times10^3$ cells/cm$^2$ and incubated in a $CO_2$ incubator (at 37° C., 5% $CO_2$) for 3 days. The medium was Dulbecco's modified Eagle medium supplemented with 10% fetal bovine serum (DMEM+10%FBS).

After incubation, culture supernatant in the culture flask was removed by aspiration, and then the remainder was treated by irradiating 10kGy- and 25kGy- electron beam at 4° C.

Epidermal cells collected from human skin were inoculated in the culture flask at $1\times10^4$ cell/cm$^2$. The medium was Green medium supplemented was 3% fetal bovine serum.

After that, epidermal cells were adhered and proliferated in the culture vessel. The epidermal cell sheet could be prepared. 3T3 fibroblasts were observed to proliferate in the culture vessel which had not been treated by irradiating electron beam, but not observed in the culture vessel treated by irradiating electron beam.

What is claimed is:

1. A method for adhering and proliferating epithelial cells, which comprises the steps of:
   inoculating, culturing and then treating by a treatment selected from freezing, drying and irradiating, in a culture vessel, fibroblasts derived from a mammal,
   separating the treated fibroblasts from said culture vessel on which the fibroblasts were cultured and treated, so as to leave an extracellular matrix on a surface of said culture vessel, and then
   inoculating and culturing the epithelial cell in said culture vessel.

2. The method according to claim 1, wherein 50% or more of the treated fibroblasts are separated from the culture vessel.

3. The method according to claim 1, wherein the treated fibroblasts are separated from the culture vessel entirely.

4. The method according to claim 1, in which said epithelial cells are epidermal cells.

5. The method according to claim 1, wherein said fibroblasts are treated by at least one selected from the group consisting of β ray, γ ray, X-ray, electron beam and UV ray.

6. The method according to claim 1, wherein said treating step of fibroblasts comprises repeating one treatment selected from the group consisting of freezing, drying and irradiating.

7. The method according to claim 1, wherein said treating step of fibroblasts comprises repeating exposure to at least one selected from the group consisting of β ray, γ ray, electron beam, UV ray and X-ray.

8. The method according to claim 1, wherein said fibroblasts are treated by a combination of at least two treatments selected from the group consisting of freezing, drying and irradiating.

9. The method according to claim 1, wherein fibroblasts are treated by at least one selected from the group consisting of β ray, γ ray, electron beam, UV ray and X-ray.

10. The method according to claim 1, wherein said fibroblasts are 3T3 mouse embryo fibroblasts.

11. The method according to claim 1, wherein the treated fibroblasts are separated entirely from said culture vessel by rinsing the culture surface with an isotonic solution.

* * * * *